(12) United States Patent
Kakko

(10) Patent No.: US 8,910,636 B2
(45) Date of Patent: Dec. 16, 2014

(54) SUPPORT HARNESS

(75) Inventor: Timo Kakko, Helsinki (FI)

(73) Assignee: Relaxbirth Oy, Espoo (FI)

( * ) Notice: Subject to any disclaimer, the term of this patent is extended or adjusted under 35 U.S.C. 154(b) by 126 days.

(21) Appl. No.: 13/389,208

(22) PCT Filed: Jul. 29, 2010

(86) PCT No.: PCT/FI2010/050611
§ 371 (c)(1),
(2), (4) Date: Feb. 6, 2012

(87) PCT Pub. No.: WO2011/015710
PCT Pub. Date: Feb. 10, 2011

(65) Prior Publication Data
US 2012/0132213 A1    May 31, 2012

(30) Foreign Application Priority Data
Aug. 7, 2009  (FI) ..................................... 20095830

(51) Int. Cl.
A61G 15/00 (2006.01)
A47L 3/04 (2006.01)
A01K 37/00 (2006.01)
A61F 5/37 (2006.01)

(52) U.S. Cl.
CPC .................................... A61F 5/3784 (2013.01)
USPC ............................... 128/845; 182/3; 119/712

(58) Field of Classification Search
USPC .......... 128/845, 846, 869–876; 119/712, 769;
119/770; 482/142, 143; 2/44–45; 180/3–6;
602/32–40
See application file for complete search history.

(56) References Cited

U.S. PATENT DOCUMENTS

| 2,758,769 | A | | 6/1953 | Nunn et al. |
| 2,817,393 | A | | 7/1954 | Mitchell |
| 2,979,028 | A | * | 4/1961 | Zakely ............................. 182/3 |
| 3,191,599 | A | | 6/1965 | Kendell |
| 3,466,090 | A | | 12/1967 | Posey |
| 3,559,932 | A | * | 2/1971 | Ternes ...................... 244/151 R |
| 5,379,725 | A | * | 1/1995 | Roberson et al. ............. 119/770 |
| 5,540,239 | A | | 7/1996 | McClellan |
| 5,957,091 | A | * | 9/1999 | McDonald et al. ........... 119/770 |
| 6,253,874 | B1 | * | 7/2001 | Casebolt et al. .................. 182/3 |
| 6,857,430 | B2 | * | 2/2005 | Morris .......................... 128/869 |
| 7,357,099 | B2 | * | 4/2008 | Smith et al. ................... 119/771 |
| 8,282,536 | B2 | * | 10/2012 | Latronica ..................... 482/121 |

FOREIGN PATENT DOCUMENTS

| BE | 1 002 357 A7 | 1/1991 |
| CA | 2 228 930 A1 | 9/1999 |
| GB | 2 274 049 A | 7/1994 |
| JP | 9047521 A | 2/1997 |
| WO | WO 2009/138548 A1 | 11/2009 |

* cited by examiner

Primary Examiner — Kim M Lewis
Assistant Examiner — Tarla Patel
(74) Attorney, Agent, or Firm — Muncy, Geissler, Olds & Lowe, P.C.

(57) ABSTRACT

This publication discloses a support harness, which can be used particularly to support a woman in labor during childbirth, but also, for example, to increase the support and comfort of persons and patients using a wheelchair, and for similar purposes. An attenuator (5, 7, 10, 14), which is based on the friction between two belts, is fitted, between the attachment elements (9-13) and the shoulder straps (3, 4), to the support harness, which comprises attachment elements (9-13), for attaching to a chair, birthing frame, or other support point, and two shoulder straps (3, 4), which are placed around the shoulders of the person being supported.

7 Claims, 3 Drawing Sheets

DETAIL A

SUPPORT HARNESS

TECHNICAL FIELD

The invention relates to a support harness, which can be used particularly to support a woman in labour during childbirth, but also to support and increase the comfort of, for example, people and patients using wheelchairs, and for similar purposes.

BACKGROUND

It is difficult to support a woman in labour, especially in the second stage of labour, or if complications arise, when quickly obtaining support may be of primary importance. Various types of chairs and auxiliary devices are available for women in labour, but many difficulties are associated with their use and usually they are only suitable for use in a single labour position. The chairs and auxiliary devices are usually located in the room farther from the childbirth bed and cannot be safely used on the bed. It is also difficult to support someone in a wheelchair or a seat in a vehicle, if for some reason they cannot keep themselves in a normal sitting position. Support can be provided using a waist belt or a three-point belt like a seat belt, but it is difficult to form support that is both sufficiently supporting and at the same time flexible. If the support is sufficiently tight, it will limit movement and feel oppressive. On the other hand, support that is too loose will not necessarily prevent falling from the chair, or the person being supported from slumping, either due to his/her own movement, or the movement of the chair/seat. Particularly when being moved downhill in a wheelchair or child's pushchair, the person sitting will feel insecure without a support harness. Support harnesses are needed in the care of the elderly and invalids, as well as in general health care. The same problems of the relation between tightness and looseness also relate to supporting a woman in labour, but even more so, because in the second stage of labour large forces are used. It must be possible to remove the support, or alter it rapidly, and the woman in labour must also be able to detach herself from the support or harness, so that it will not feel oppressive. The support, for example a support harness, must also not squeeze or press on the woman uncomfortably at any stage.

For the reasons described above, support harnesses used especially in childbirth are difficult to implement satisfactorily.

SUMMARY

The invention is intended to create a support harness that is more suitable than previous solutions for supporting a person in a sitting, or sitting-like position, and particularly for use in childbirth.

The invention is further intended to create a support harness, which is suitable for supporting a person with limited mobility, a patient or other person requiring support, in a seat, such as a wheelchair or the seat of a vehicle.

The invention is based on the support harness, which comprises attachment elements for attaching to a chair, birthing frame, or other support point, and two shoulder straps, which can be placed around the shoulders of the person being supported, being equipped with an attenuator, which is fitted between the attachment elements and the shoulder straps and is based on the friction between two belts.

According to one preferred embodiment of the invention, the attenuator comprises a belt loop, which is arranged to run through a first ring, and a band fitted inside the belt loop, one end of the band being arranged to run through the first ring inside the belt loop and its second end being attached to a second ring, the belt loop being arranged to also run through this second ring.

According to one embodiment, there are quick-release locks in the shoulder straps, which are located in loops, so that they can be easily opened in front of the user.

Further, according to one preferred embodiment, the support harness includes at least one attachment point for attaching auxiliary harnesses, body and limb and other additional supports, as well as other possible additional equipment.

More specifically, the support harness according to the invention is characterized by what is stated in the independent Claim.

Considerable advantages are gained with the aid of applications of the invention.

The support harness according to the invention does not prevent too much normal movement by the user, but creates sufficient support to increase safety. The attenuator belonging to the harness prevents sudden stopping movements and thus reduces the danger of whiplash injury to the head and neck. This is especially important in the case of an injured person, or fainting taking place during labour and, for example, should the user fall asleep when using a wheelchair, chair, or recliner, or if a wheelchair collides with something, for example, when being moved down a slope. The support harness according to the invention does not press over the user's chest or the user's chest. This is important in terms of comfort, particularly during childbirth, as the breasts and mammary glands of a woman giving birth can be very tender. One essential feature is that the support is based on two loops running around the shoulders. Freeing oneself from these loops is already reasonably easy, so that the harness does not create an oppressive feeling, which can be a problem in solutions that are more tightly attached. In addition, the shoulder-strap loop is preferably equipped with quick-release locks, so that the user can, even with a weak hand, open the shoulder-strap lock if they wish and release themselves from the harness. The easy detaching particularly helps a woman in labour to change position. The position may have to be changed due to various emergencies, or the woman herself may wish to change position as the birth progresses and the second stage continues. It is then advantageous for the woman to be as free as possible to move, with the midwife only assisting her if she wishes, or when necessary.

The harness can be manufactured from a dirt-rejecting, soft, and pleasant material, and be equipped, for instance with gel pads to increase comfort in use. The material of the belts must be, however, non-shrink, non-stretch, and withstand washing in hospital conditions, as well as disinfection in a sufficiently hot and acid or alkali environment. In other, non-hospital uses, disinfection resistance is not necessarily required, but it must be possible to wash the harness using at least home methods.

Although considerable demands are set for the materials of the harness, the materials need not be expensive and manufacture of the harness is reasonably easy. It is therefore no more expensive to manufacture than other similarly demanding special products.

BRIEF DESCRIPTION OF THE DRAWINGS

In the following, the invention is examined with the aid of examples and with reference to the accompanying drawings.

DETAILED DESCRIPTION OF EMBODIMENTS

One of the most important uses of the invention relates to supporting a woman in labour during childbirth. The harness according to the invention can be attached, in suitable parts, to various childbirth beds or supports, but it is especially suitable for use in connection with the birthing support disclosed in the international patent application PCT/FI2008/050504. A description of the aforementioned birthing support can be found in the international patent application, so it is unnecessary to describe the device here.

A second important application of the invention is to support in a sitting position the elderly, partly paralysed or tetraplegic patients, the permanently disabled, sick persons, narcoleptics, injured persons, or persons otherwise requiring support when sitting, as well as to prevent their sudden movement when stationary and when being moved.

In the present application, the terms sitting position and similar positions refer to positions, in which the back is at least partly supported upwards and at least part of the weight is supported on the buttocks.

Figure 1:
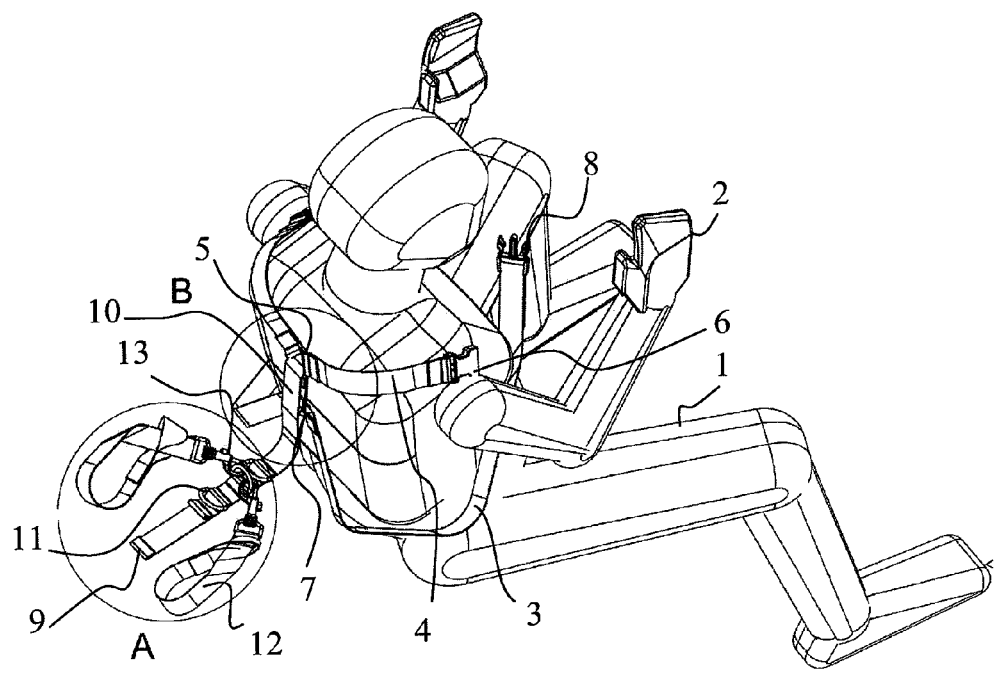
FIG. 1 shows schematically one harness according to the invention, being partly worn by a user.
Figure 2:
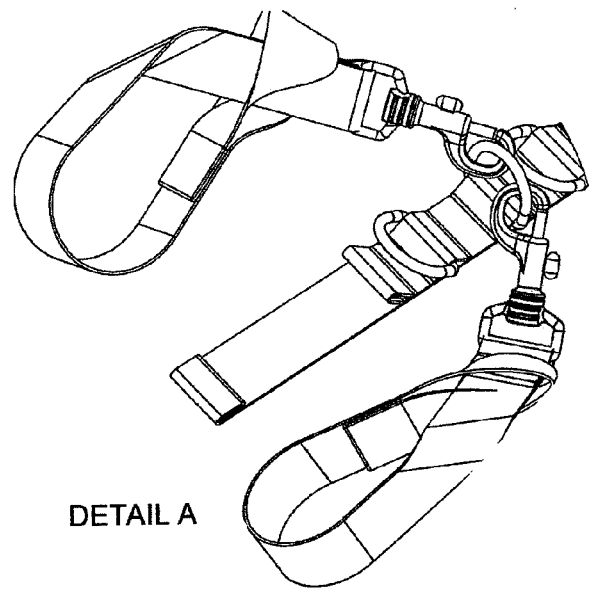
FIG. 2 shows the harness according to FIG. 1 detached and opened.
Figure 3:
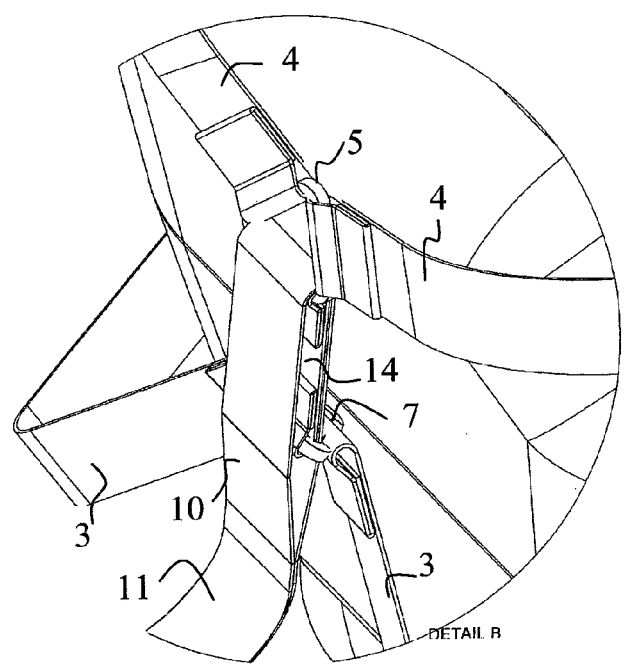
FIG. 3 shows a detail A of FIGS. 1 and 2.
Figure 4:
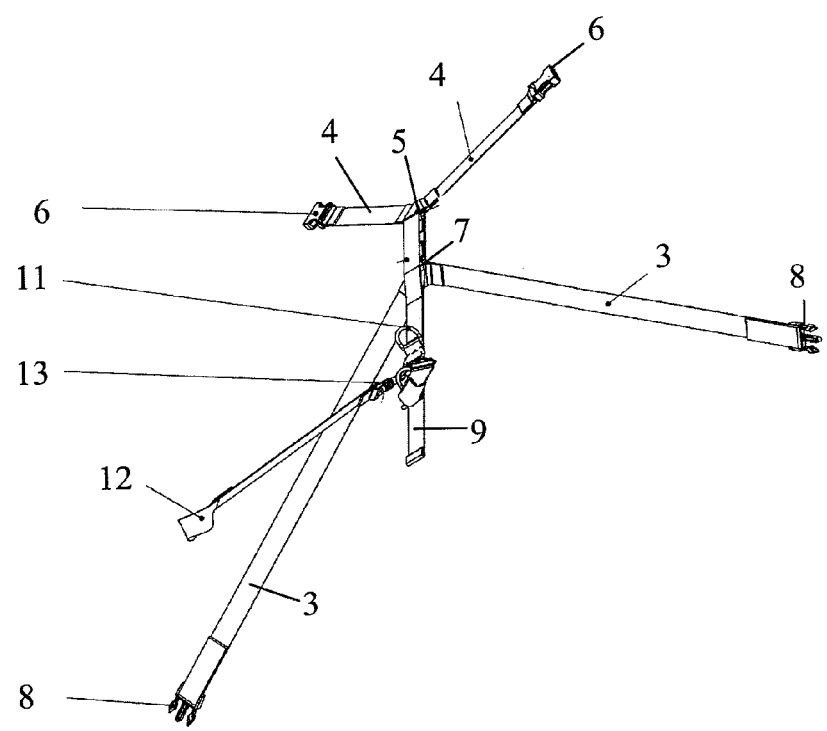
FIG. 4 shows a detail B of FIGS. 1 and 2.

The embodiment of the invention shown in FIGS. 1-4 comprises two integrated parts, an attachment part (FIG. 2) to be attached to a wheelchair, seat, or birthing frame, and a harness part to be attached to the person 1. The harness part comprises two shoulder straps, which consist of two loop parts 3, 4 made from a flat belt. The first end of the upper loop part 4 is attached to a triangular ring 5, and the female piece 6 of the locking device is at the free end of the loop part. The upper loop part 4 is arranged to run over the outer part of the user's shoulders. The first end of the lower loop part 3 too is attached to a ring 7 and has the male piece 8 of the locking device at its free end. The lower loop part 3 is arranged to run under the armpit, thus creating a support loop running around the shoulder by using the locking device 6, 8 to join the loop parts 3, 4. The lower and upper parts of each shoulder loop 3, 4 are attached symmetrically to the same rings 5 and 7. These rings are connected by a loop 10 at the end of a main belt 9, which loop thus belongs to both the harness part and the attachment part.

In this embodiment, three attachment rings 11 are attached at suitable intervals to the main belt 9. Attachment straps 12, by which the support harness is attached, for example to a birthing support, bed, or wheelchair, are attached to one of these rings. In this case, the ends of the straps have loops for attachment, but any suitable form of attachment can be used, such as various buckles, locks, catches, or even a Velcro attachment. The essential point is that the manner of attachment must be easy to use and reliable and meet the appropriate hygienic requirements. Obviously, home-use requirements will differ totally from those in, for example, a hospital delivery room, or in geriatric care.

One important feature of the invention is the fabric-loop attenuator, which slows the forward movement of the person supported. This attenuator is constructed inside the loop 10 of the main belt 9. The main-belt 9 loop runs through a triangular ring 5, to which the upper loop parts 4 of the shoulder straps are also attached. A band 714, with loops at both ends, is fitted inside the main-belt loop 10. The first loop runs around the triangular ring 5 inside the main-belt loop and the band 7-14 extends away from the triangular ring 5 also inside the main-belt loop 10. The attachment ring 7 of the lower shoulder-straps 3, which can also be triangular, runs through the second loop at the other end of the band 14. Thus, both the main-belt loop 10 and the band loop of the band 14 run through the attachment ring 7, and the attachment ring 7 guides the band 14 against the inner surface of the main-belt loop. Thus, the first end of the band 14 is fixed in the triangular ring 5, to which both the upper parts 4 of the shoulder straps and the main-belt loop 10 are attached, the second end being attached to the attachment ring 7 moving in the main-belt loop 10. Thus, the attachment ring 7 can move over the main-belt loop 10 for the distance set by the length of the band 14.

The support-harness construction described above can vary from that described. Triangular rings are advantageous for jointing three belts, but of course other ring shapes can be used. At least in the attenuator part and the parts supporting the person being supported, the belts should be flat, to keep the surface pressure small and use comfortable. The harness's locks and connectors can obviously be chosen from a wide range of existing solutions. However, these parts must be easy to use and reliable. It can also be envisaged that a separate back part is formed for the harness, to which the necessary belts are attached. In this way, the appearance of the harness can be varied to correspond better to normal clothing. Various rain or moisture-resistant covers can also be attached to the harness, which can be used when moving a sitting person outdoors.

The support harness's belts and bands must be of a non-shrink material, such as polypropylene fabric or similar. The locks, rings, and other connector components too must withstand washing and, if necessary, hospital-standard soaking and decontamination, as well as hot-air/cold-air drying. In hospital conditions, the locks and loops must resist the surface-disinfection agents generally used in hospitals, as well as secretory disinfection. As examples, mild detergent solutions presently used have a pH of about 7-8.3 or a corresponding degree of acidity downwards, or an app. 5000 ppm or 20-25% Klorilli-solution or phenol used in a secretory disinfection.

It is also essential that no seam or connector touches the person, his/her exposed or clothed skin, or rubs on a shoulder, clavicle, or armpit. Especially in long-term use, the support harness can be of a dirt-resistant, padded (e.g., gel padding) material. The locks and rings can be made of polymer materials, composites, or suitable metals and can be coated with a dirt- and operating-strain-resistant coating.

In use, the harness according to the invention operates in the following manner.

The harness is put on by placing the upper parts 3 of the shoulder loops over the shoulders and connecting the lower part to the upper part with the locking element. The position of the locking element is dimensioned so as not to press on the user, but to be easily attachable and detachable using the opposite hand. Thus, the user can easily put on, adjust, tighten, and take off the harness without help. Because the harness can be easily taken off by the user himself/herself, its use is not oppressive and the user need not fear being trapped in the harness. The harness also does not prevent the free movement of the hands, arms, and shoulders.

The attachment part of the harness can be already attached, by loops 12 or other attachment components, to a birthing device, a seat, a chair, or the handles of a wheelchair, or an assistant can make the attachment once the user has put the harness on. In this case, there are three rings at suitable intervals on the main belt 9. The loops 12 are attached to these rings 11, at a suitable point according to the user's height. These so-called adjustment loops permit the harness to be adjusted according to the size and height of the woman in labour/user. The adjustment tolerance includes several stainless/galvanized metal rings (or other similar rings) in the back part or main part of the support harness itself, allowing attachment to a suitable point. In principle, even one attachment ring is enough, but two or more easily increase ease of use through adjustability. The optimal location of the main belt of the attachment part is between the user's shoulder blades, where it will not cause a chafing feeling, even when the user leans backwards.

Once the support harness has been put on, the attenuator band 14 should be pulled out to its full length. If the person in the harness now falls or tilts forwards, the lower parts 3 of the shoulder straps tighten, tightening the ring 7 and band 14 against the inner surface of the main-belt loop 10. The upper parts 4 of the shoulder loops, for their part, pull on the triangular ring 5 and main-belt loops 10 and band 14 running through it. The main-belt loop 10 now slides in the ring 7 of the lower ends of the shoulder straps and the band 14 presses against the main-belt loops 10. The friction between the loop 10 and band 14 and the resistance of the loop 10 in the ring 7 oppose the movement, thus slowing the movement. However, the distance between the attachment rings of the shoulder-strap lower 3 and upper parts can decrease and the loop 10 of the main part can straighten, permitting a forward movement corresponding to the free-movement length of the band 14. Because friction and inertia slow the movement, the user's movement does not stop suddenly but is damped. The damping effect is also regulated automatically, as the faster the movement and the greater the force pulling on the rings 5, 7 the more tightly the parts of the attenuator system press against each other and the greater the friction created. Using this attenuator system, the user's relatively free movement of the upper and lower body can be combined with safe stopping in a situation of uncontrolled movement.

If the user wishes to take off the harness, he/she can easily simply open the shoulder-strap locks and the harness will be off entirely. It can also be easily opened by an assistant.

Accessories can be attached to the support harness. These can be, for example, accessories used in connection with known harnesses and, for instance, in connection with wheelchair use, bags, cases, and attachments for various requisites using when shopping, fishing, and on outdoor expeditions. After all, there are now trekking and fishing destinations available to wheelchair users. Similarly, if additional support, e.g. lateral support, is required, auxiliary attachment elements or harnesses can be used. The support harness should have suitable attachment points for such additional accessories or devices. The number of attachment points depends on the desired level of adaptability and the need for multiple uses, but to be able to use accessories at all there must be at least one attachment point. As such, the number of attachment points is not limited, and the harness's attachment rings and even buckles can be used as attachment points if suitable.

On the basis of the examples given above, it is obvious that, within the scope of the invention numerous solutions differing from the embodiments described above can be implemented. Thus, it is not intended to restrict the invention to concern only the examples presented above, instead the patent protection should be examined to the full extent of the accompanying Claims.

The invention claimed is:

1. A support harness for supporting a person in a position similar to a sitting position, comprising:
   attachment elements for attachment to a support point, and
   two shoulder straps, which can be fitted around the shoulders of the person being supported, attached to the attachment elements,
   wherein an attenuator, which is based on friction between two belts, is fitted between the attachment elements and the shoulder straps, the attenuator being positioned on a backside of the person, and
   the attenuator comprises an attachment ring, a main-belt loop and a band including a band loop and having a first end fixed to a triangular ring,
   ends of the shoulder straps are attached to the attachment ring and to the triangular ring, and
   both the main-belt loop and the band loop run through the attachment ring so that the attachment ring guides the band against an inner surface of the main-belt loop thereby a frictional force is generated between the band and the main-belt loop.

2. The support harness according to claim 1, wherein the attenuator comprises:
   the triangular ring, through which the main-belt loop is arranged to run, and to which a first end of the shoulder straps can be attached,
   the attachment ring, which is arranged to move freely around the belt of the belt loop, and to which a second end of the shoulder straps can be attached, and
   the band, fitted inside the main-belt loop, includes a second end attached to the attachment ring.

3. The support harness according to claim 1, wherein the shoulder straps consist of two parts and at least one end of each part is a locking element to be attached to the corresponding locking element at the end of the other part.

4. The support harness according to claim 1, wherein the attachment elements comprise elements for attaching to a birthing accessory.

5. The support harness according to claim 1, wherein the attachment elements comprise elements for attaching to a wheelchair.

6. The support harness according to claim 1, wherein the attachment elements comprise elements for attaching to a seat in a vehicle.

7. The support harness according to claim 1, further comprising at least one attachment means for attaching additional requisites to the support harness.

\* \* \* \* \*